United States Patent [19]

Sinn

[11] Patent Number: 5,228,565
[45] Date of Patent: Jul. 20, 1993

[54] PACKAGE AND METHOD OF LOADING FOR RESILIENT SURGICAL SUTURES

[75] Inventor: Hans-Jurgen F. Sinn, Fairfield, Conn.

[73] Assignee: United States Surgical Corporation, Norwalk, Conn.

[21] Appl. No.: 842,525

[22] Filed: Feb. 26, 1992

[51] Int. Cl.⁵ ............................................. A61B 17/06
[52] U.S. Cl. ..................................... 206/63.3; 53/430; 53/473; 206/227; 206/380
[58] Field of Search ............... 206/63.3, 63.5, 227, 206/380, 388, 303, 389, 403, 408, 409, 461, 523; 53/409, 449, 430, 473

[56] References Cited

U.S. PATENT DOCUMENTS

| | | |
|---|---|---|
| 2,617,523 | 11/1952 | Zoller . |
| 2,938,624 | 5/1960 | Runkel et al. ............ 206/63.3 |
| 3,062,372 | 11/1962 | Egler et al. . |
| 3,127,992 | 4/1964 | Horine ................... 206/63.3 |
| 3,167,895 | 2/1965 | Egler et al. . |
| 3,185,299 | 5/1965 | Trainer ................... 206/63.3 |
| 3,280,971 | 10/1966 | Regan, Jr. . |
| 3,301,393 | 1/1967 | Regan, Jr. et al. ........... 206/409 |
| 3,444,994 | 5/1969 | Kaepernik et al. . |
| 3,731,793 | 5/1973 | Hagel .................... 206/63.3 |
| 3,876,068 | 4/1975 | Sonnino . |
| 3,939,969 | 2/1976 | Miller et al. . |
| 3,959,947 | 6/1976 | Sonnino . |
| 4,142,628 | 3/1979 | Marocco et al. . |
| 4,183,431 | 1/1980 | Schmidt et al. ............ 206/63.3 |
| 4,284,194 | 8/1981 | Flatau . |
| 4,424,898 | 1/1984 | Thyen et al. . |
| 4,961,498 | 10/1990 | Kalinski et al. . |
| 4,967,902 | 11/1990 | Sobel et al. . |

FOREIGN PATENT DOCUMENTS

0662417 4/1963 Canada .................... 206/63.3

Primary Examiner—Jimmy G. Foster
Attorney, Agent, or Firm—Thomas R. Bremer; Peter G. Dilworth; Rocco S. Barrese

[57] ABSTRACT

A package is provided for receiving and retaining at least one resilient surgical suture arranged in a coil configuration. The package is formed with a loading port which defines a radially unobstructed passageway through which a resilient surgical suture coil may be loaded and thereafter caused to uncoil and expand radially outward into a retaining channel. The package may include needle park means for securely maintaining armed sutures in a manner for ready removal.

26 Claims, 8 Drawing Sheets

PACKAGE AND METHOD OF LOADING FOR RESILIENT SURGICAL SUTURES

BACKGROUND OF THE INVENTION

1. Field of the Invention

The invention relates to a new and improved package for retaining resilient surgical sutures and a method for loading the sutures into the package, whereby the resiliency of the suture material enables the sutures to be self-loaded into the package.

2. Description of the Related Art

Many monofilament surgical sutures possess certain mechanical characteristics such as stiffness and a tendency to be wire-like and resilient. In the past, such sutures have been retained in packages manufactured in such a manner so as to enable the formation of upstanding projections within the package body around which the sutures could be wound so as to be captured in a peripheral storage channel.

Prior art packages manufactured in such a manner include U.S. Pat. No. 4,424,898 entitled "Needle and Suture Holder and Package" which issued to Thyen et al. on Jan. 10, 1984 which discloses a package for retaining a plurality of sutures. The package basically comprises a dish-like holding member having an outer peripheral wall defining the outside wall of a retaining channel and a plurality of spaced apart upstanding projections opposed adjacent to the outer peripheral wall and defining an inside wall of a retaining channel. Sutures may be disposed within the channel by wrapping them about the upstanding projections in such a manner as to fill the channel with sutures. The package further comprises an upper needle-holding holding member having a planar surface which mates with the dish-like holding member in such a manner so as to enclose the retaining channel. The needle-holding member includes a plurality of needle-holding means disposed in spaced relationship upon the planar surface thereof for securely retaining a plurality of suture needles.

U.S. Pat. No. 4,961,498 entitled "Oval Wrap Suture Package" which issued to Klinski et al. on Oct. 9, 1990 discloses a molded two-piece suture package which defines an oval channel within which sutures may be wound. In particular, the suture package comprises a tray member having an oval dish-like area formed thereon, a bottom member enclosed within the dish-like area and having an outer peripheral wall and a plurality of inner lug members which in combination define a suture wrapping channel, and a top member disposed over the bottom member and fastened thereto having a central depression which defines an inner wall having a plurality of notches for being interfingered with the lug members on the bottom member to define an oval channel within which sutures may be wound.

U.S. Pat. No. 4,967,902 entitled "One Piece Nov. 6, 1990 discloses a one piece surgical suture package. The package basically comprises a suture holder having a rounded peripheral channel for retaining a suture. The channel is formed with an open side to which are attached a plurality of hinged doors. After the suture is wound into the channel the doors may be folded over the channel and locked into place so as to secure the suture in the channel. Thereafter, the suture needle can be placed in a parking means disclosed within the center of the storage channel.

These prior art suture retainer packages have not taken advantage of the resiliency of certain suture materials to aid in the loading of the package. Instead, prior art retainers have employed winding projections which may cause sutures to take an undesirable set when loaded into the package body.

Retainers wherein a suture can be automatically fed through a notch provided in a partially assembled retainer to coil on itself are described in U.S. Pat. No. 4,142,628 entitled "Direct Dispensing Suture Package For A Multiple Of Sterile Surgical Sutures With or Without Needles Attached" which issued to Marocco et al. on Mar. 6, 1979.

It has been found that when a resilient monofilament surgical suture made of catgut or a similar material is inserted into a package in a coiled configuration, the resilient suture will tend to uncoil within the package and expand radially outward so as to conform generally to the shape of the enclosure. In accordance with this principle, it is desired to provide a suture retainer package which does not necessitate the formation of upstanding projections around which sutures may be wound to be loaded into the package. Instead, it is an object of the subject invention to provide a package for retaining at least one resilient surgical suture which permits the suture to be essentially self-loaded into a retaining area.

Stated differently, it is an object of the subject invention to provide a suture retainer package into which a resilient suture coil may be loaded and thereafter caused to uncoil and expand radially outward within the package so as to be retained therein.

It is another object of the subject invention to provide a suture retainer package which can be manufactured relatively inexpensively.

It is still another object of the subject invention to provide a suture retainer package for retaining a plurality of resilient surgical sutures.

It is yet another object of the subject invention to provide a suture retainer package which enables a plurality of resilient suture coils each having a needle affixed to one end to be loaded into the package in such a manner to enable ready removal.

It is yet a further object of the subject invention to provide a package for retaining a plurality of resilient surgical suture coils which when packed do not take an undesirable set.

SUMMARY OF THE INVENTION

The suture retainer package of the subject invention is provided for receiving and maintaining for ready removal at least one resilient surgical suture arranged in a coiled configuration. The suture retainer package basically comprises peripheral suture retaining means having at least a top and a bottom portion being enclosed at a radially distal edge. The top portion has a loading port formed therein which defines a radially unobstructed passageway for receiving a resilient suture coil into the peripheral retaining means.

The package may further comprise needle park means for releasably retaining at least one needled suture. The needle park means may be provided on the top portion of the package or in the alternative on the bottom portion. Further still, the needle park means may be disposed on a platform which may extend radially into the loading port formed in the top portion of the package.

The package may be loaded by inserting the resilient suture coil into the loading port and thereafter causing the suture to uncoil and expand radially outward into the suture retaining means.

In a preferred embodiment of the suture retainer package of the subject invention, the package comprises a top portion which is preferably vacuum formed from polyethylene. The top portion includes an upstanding peripheral wall of elliptical configuration which forms a loading port defining a radially unobstructed passageway for receiving at least one resilient suture coil into the package. A lower wall extends radially outward from the peripheral wall and an upper wall extends radially inward from the peripheral wall. The package further comprises a bottom portion which is preferably vacuum formed from polyethylene and which may be sonically welded to the lower wall of the top portion at a radially distal edge thereof so as to construct the retainer package.

The suture retainer package may further comprise needle park means which is preferably a foam sponge disposed in a housing associated with the bottom portion of the package. In this instance the needle park means would extend upwardly into the loading port.

To load the preferred embodiment of the retainer package of the subject invention a resilient surgical suture in a coil configuration may be inserted into the loading port formed in the top portion of the package and thereafter the suture may be caused to uncoil and expand radially outward into the retainer package so as to be accommodated therein. Thereafter, the needled end of the suture could be engaged in the needle park means in such a manner so as to permit easy removal.

In another embodiment of the subject invention the retainer package comprises a substantially planar top portion and a substantially planar bottom portion, both of which are preferably made from Tyvek ®, a woven material which is impervious to bacteria. The material of the package may be coated with an adhesive. The top portion of this package is provided with a circular aperture which forms a loading port defining a radially unobstructed passageway through which a resilient surgical suture in a coil configuration may be loaded into the retainer package. The top portion may be sonically welded to the bottom portion of the package along a peripheral edge thereof to enclose the retaining means on all sides.

This embodiment of the retainer of the subject invention may further comprise needle park means preferably made of a plastic material and having at least one arm depending orthogonally from a base. The arm may be provided with a plurality of spaced apart apertures for receiving and retaining a plurality of curved suture needles. In that instance, the top portion of the package would include at least one engaging slot for receiving the arm of the needle park member in such a manner so that the base is maintained between the top portion and the bottom portion of the package when the package has been constructed.

This embodiment of the retainer package of the subject invention may further include needle protector means. The needle protector means would comprise a top member disposed over the top portion of the package for covering the suture needles, and a bottom member disposed beneath the lower member of the package. The needle protector means can be made of styrene and can be secured to the retainer package by sonically welding the members to one another through apertures which may extend through the package adjacent an edge thereof. The top member of the needle protector means can be lifted to gain access to the suture needles and thereafter released to resiliently return to a protective position over the needle park.

To load this embodiment of the retainer the package of subject invention, a resilient suture coil may be inserted into the loading port and thereafter caused to uncoil and expand radially outward into the package so as to be retained therein. At such a time, a suture needle may be engaged in the needle park means. Thereupon, the needle protector means can be attached to the retainer package.

In yet another embodiment of the subject invention, the suture retainer package comprises an annular channel having a substantially C-shaped cross-section formed in an injection molding process. The annular channel includes an upstanding peripheral wall forming a loading port which defines a radially unobstructed passageway for receiving resilient coiled surgical sutures into the annular channel. In addition, the package may include a planar platform extending radially into the loading port from the upstanding peripheral wall upon which needle park means may be provided.

This embodiment of the suture retainer package of the subject invention may be loaded by inserting at least one resilient suture coil concentrically into the annular loading port and thereafter, causing the resilient suture to uncoil and expand radially outward into the annular channel. Subsequently, a surgical needle can be inserted into the needle park means so as to be maintained for ready removal.

Further features of the invention will become more apparent from the accompanying drawings and the following detailed description of the invention.

BRIEF DESCRIPTION OF THE DRAWINGS

Preferred embodiments of the invention will be described hereinbelow with reference to the drawings wherein.

PREFERRED EMBODIMENT OF THE SUBJECT INVENTION

A preferred embodiment of the package for retaining resilient surgical sutures of the subject invention is illustrated in FIGS. 1-8 and is designated generally by reference numeral 10. The retainer package 10 is particularly adapted for accommodating a plurality of resilient surgical sutures 12 each initially arranged in a coil configuration, and each having an arcuate needle 14 affixed at one end which can be securely maintained in a needle park 16.

Figure 1:
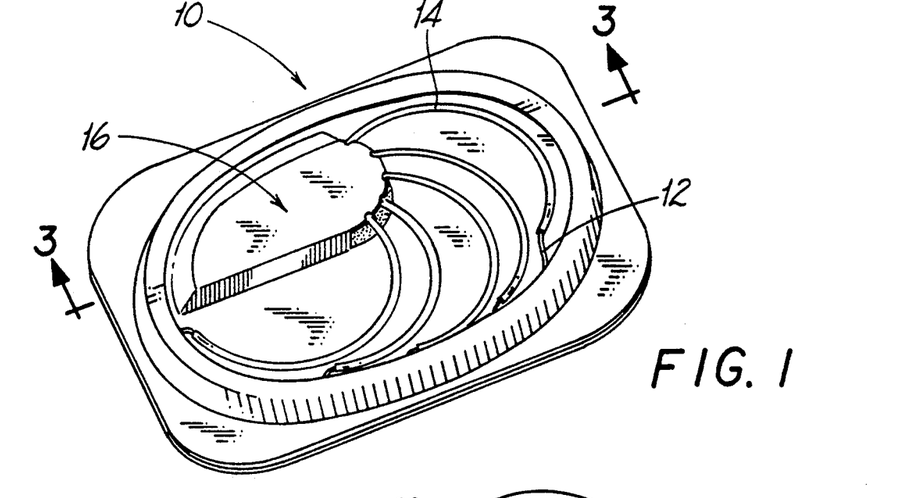
FIG. 1 is a perspective view of the preferred embodiment of the suture retainer package of the subject invention.
Figure 2:
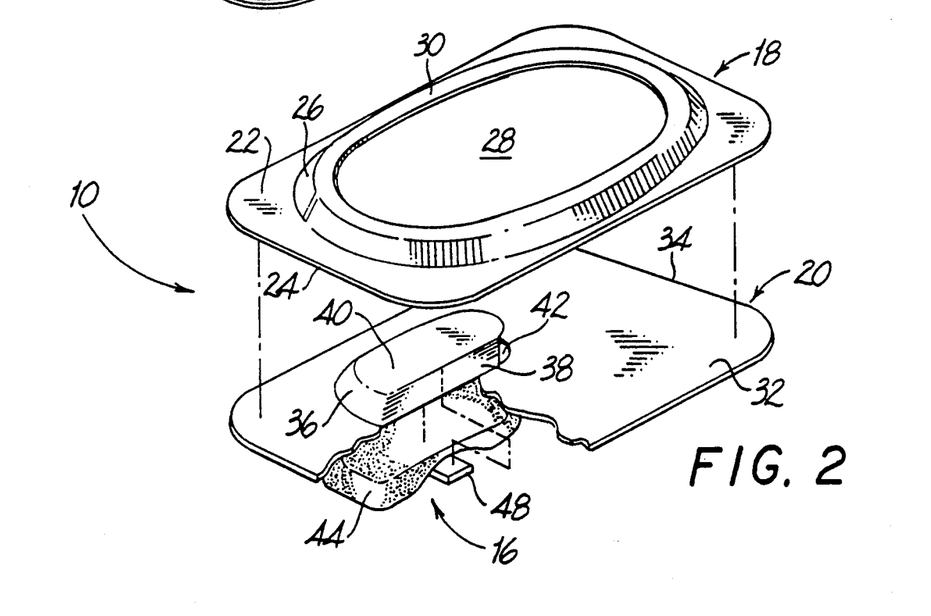
FIG. 2 is an exploded view with parts broken away of the preferred embodiment of the suture retainer package of the subject invention.

Referring to FIG. 2, the retainer package 10 of the subject invention comprises a top portion 18 and a bottom portion 20 which are both vacuum formed from polyethylene to a preferred thickness of about 0.013" such that the entire package 10 once assembled, has a thickness "t" of about 0.2". Top portion 18 includes a flange wall 22 having a radially distal edge 24. An upstanding peripheral wall 26 extends from flange wall 22 to form a substantially elliptical loading port 28 which defines a radially unobstructed passageway through which resilient surgical sutures 12 may be inserted into retainer package 10. Upstanding wall 26 is necessarily angled inwardly approximately 2.5° so as to facilitate the vacuum forming process. Furthermore, a peripheral lip 30 extends radially inward from the top of upstanding wall 26.

The bottom portion 20 of retainer package 10 includes a substantially planar plate 32 having a radially distal edge 34. Needle park 16 is formed in bottom portion 20 of retainer package 10 and includes an arcuate beveled wall 36, an upstanding wall 38, and a hood 40. In addition, an access port 42 is provided proximate to the center of loading port 28 for receiving the surgical needles 14 affixed at the end of each suture 12. A sponge member 44 is disposed in needle park 16 and is maintained therein by a brace 48.

Figure 3:
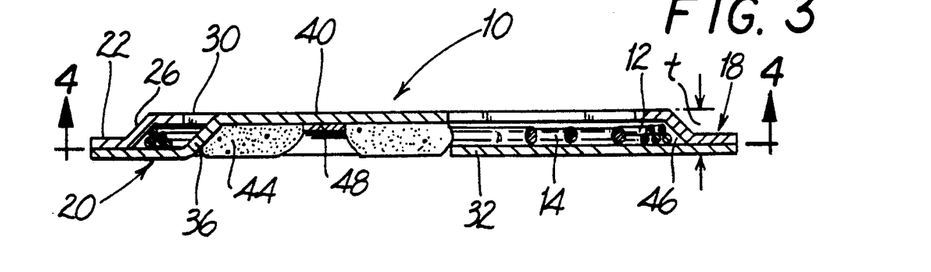
FIG. 3 is a cross-sectional view taken along line 3—3 in FIG. 1 illustrating the suture retainer package shown in FIGS. 1 and 2.
Figure 4:
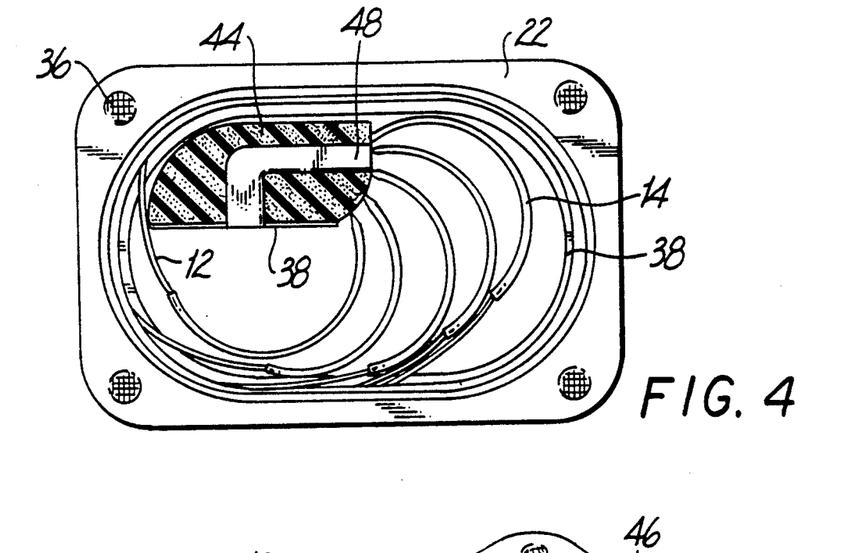
FIG. 4 is a cross-sectional view taken along line 4—4 in FIG. 3 illustrating the suture retainer package shown in FIGS. 1 and 2.

Referring to FIGS. 3 and 4, brace 48 is affixed or sonically welded to the undersurface of hood 40 of needle park 16 in such a manner as to sandwich sponge member 44 therebetween. Surgical needles 14 which are extended through access port 42 are inserted into sponge member 44 so as to be securely maintained therein.

Retainer package 10 is constructed by sonically welding the top portion 18 to the bottom portion 20 adjacent the respective radially distal edges 24 and 34 thereof at locations indicated by reference numerals 36 in FIG. 4. Once constructed, the retainer package 10 defines a peripheral channel 46 having a generally C-shaped cross-section within which a plurality of resilient surgical sutures 12 are accommodated. Moreover, peripheral channel 46 is defined by the planar plate 32 of bottom portion 20, the upstanding wall 26, and the peripheral lip 30 of top portion 18.

Figure 5:
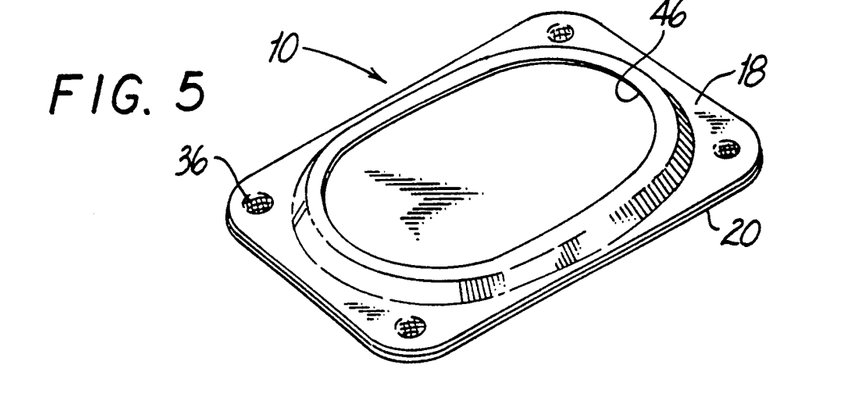
FIG. 5 is a perspective view of an alternate embodiment of the suture retaining package shown in FIG. 1.

Referring to FIG. 5 in an alternate embodiment of the suture retainer package 10, the bottom portion 20 can be formed without a needle park. In this instance, top portion 18 and bottom portion 20 would be joined to one another at weldments 36 to define the peripheral channel 46 within which a plurality of unarmed resilient surgical sutures may be accommodated.

Figure 6:
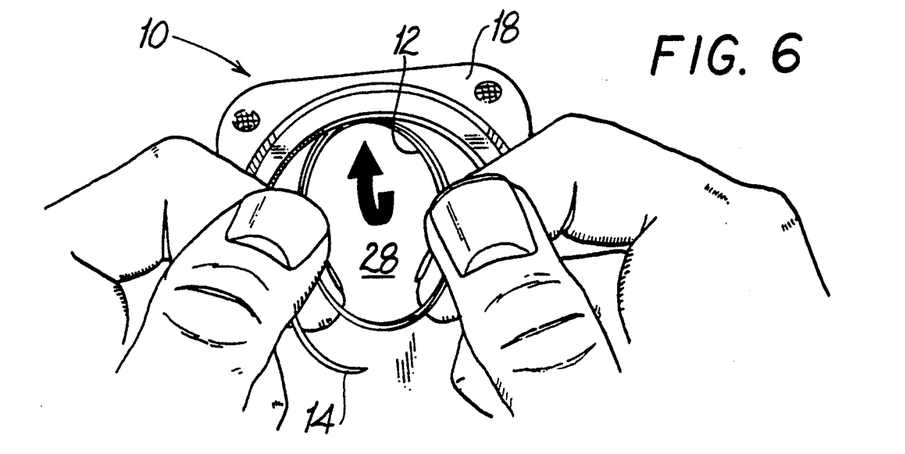
FIGS. 6–8 illustrate a method of loading a resilient surgical suture in a coil configuration into the suture retainer package illustrated in FIGS. 1 and 2.
Figure 7:
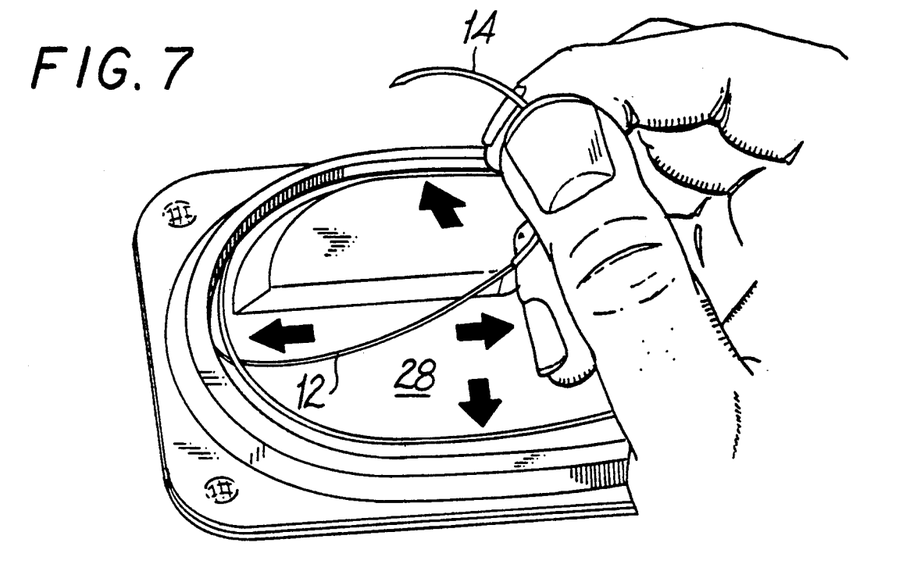
Figure 8:
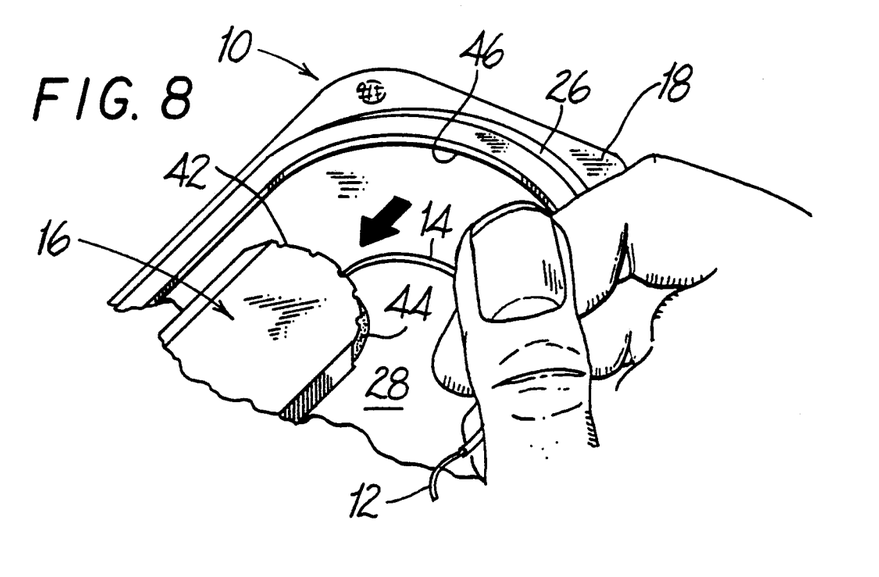

Turning now to FIGS. 6-8 the suture retainer package 10 of the subject invention is to be loaded by inserting a resilient surgical suture 12 in a coil configuration into loading port 28 formed in the top portion 18. More particularly, upon inserting suture 12 into loading port 28 a portion of the suture is directed into the peripheral channel 46 as illustrated by the indicator arrow in FIG. 6. Thereafter, the resilient suture 12 may be released and permitted to uncoil and expand unobstructedly, radially outward into the peripheral channel 46 as illustrated by the indicator arrows in FIG. 7. At such a time, a curved surgical needle 14 may be grasped and directed toward the needle park 16. Thereafter, the surgical needle 14 may be extended into the access port 42 and inserted into sponge member 44 as illustrated by the indicator arrow in FIG. 8, so as to be securely maintained therein in such a manner to permit ready removal with a surgical instrument.

Figure 9:
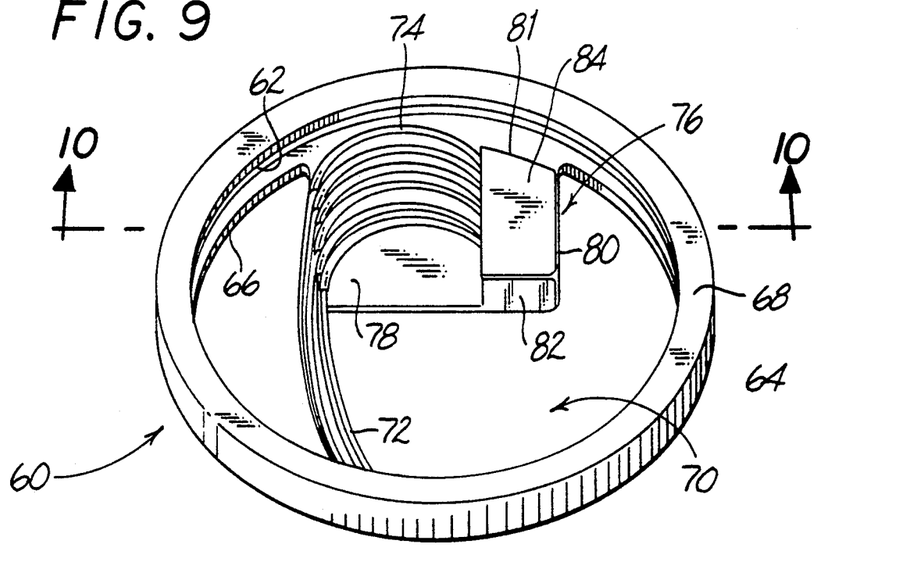
FIG. 9 is a perspective view of a second embodiment of the suture retainer package of the subject invention.
Figure 10:
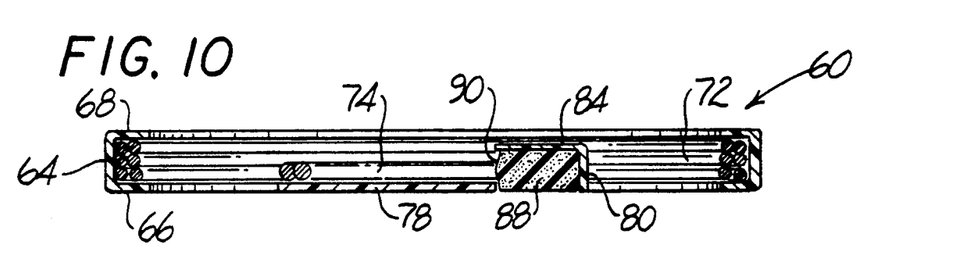
FIG. 10 is a cross-sectional view taken along line 10—10 in FIG. 9 illustrating the suture retainer package of the subject in FIG. 9.
Figure 11:
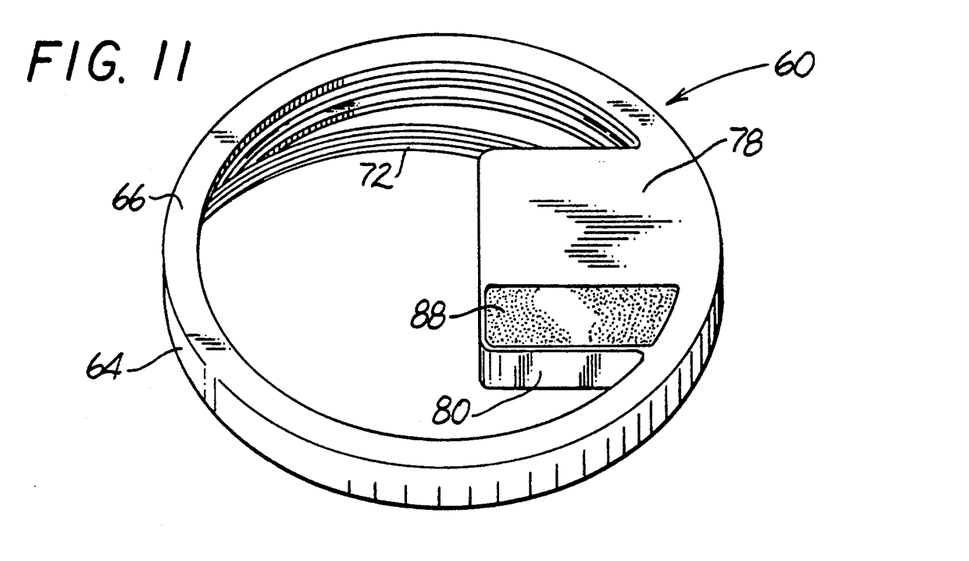
FIG. 11 is a perspective view from below illustrating the suture retainer package shown in FIG. 9.

A second embodiment of the suture retainer package of the subject invention is illustrated in FIGS. 9-11 and is designated generally by reference numeral 60. Retainer package 60 comprises an annular channel member 62 which preferably has an outer diameter of from about 3.0" to about 4.0" and which is preferably formed in an injection molding process. Channel member 62 includes an upstanding circular wall 64, a lower lip 66, and an upper lip 68 both extending radially inward from upstanding wall 64 to form a substantially circular loading port 70 which defines a radially unobstructed passageway through which armed surgical sutures 72 each having a curved surgical needle 74 affixed at one end and each arranged in a coil configuration may be loaded into the retainer package 60. Retainer package 60 further comprises a needle park 76 disposed on a planar platform 78 extending radially inward from lower lip 66 into loading port 70. Needle park 76 is defined by upstanding walls 80 and 82 and roof panel 86. A sponge member 88 is disposed in needle park 76 and is securely maintained therein by affixation to the roof 86 with glue or the like. Sponge member 88 is readily accessible through an aperture 90 which is provided opposite side wall 80.

To load the suture retainer package 60 of the subject invention, a resilient surgical suture 72 arranged in a coil configuration may be inserted concentrically into the circular loading port 70 defined therein. Upon inserting the coiled surgical suture 72 into loading port 70 a portion of the surgical suture 72 is directed into the annular channel member 62 of suture retainer package 60. Thereafter, the surgical suture coil 72 is released so as to be permitted to uncoil and expand unobstructedly, radially outward into the annular channel member 62. At such a time, surgical needles 74 may be extended through aperture 90 in needle park 76 to be inserted into the sponge member 88 and maintained therein in such a manner to permit ready removal with a surgical instrument.

Figure 12:
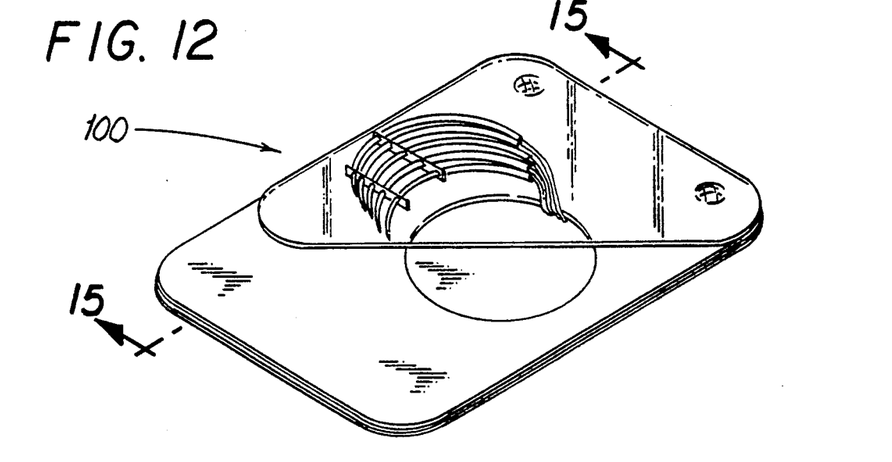
FIG. 12 is a perspective view of a third embodiment of the suture retainer package of the subject invention.
Figure 13:
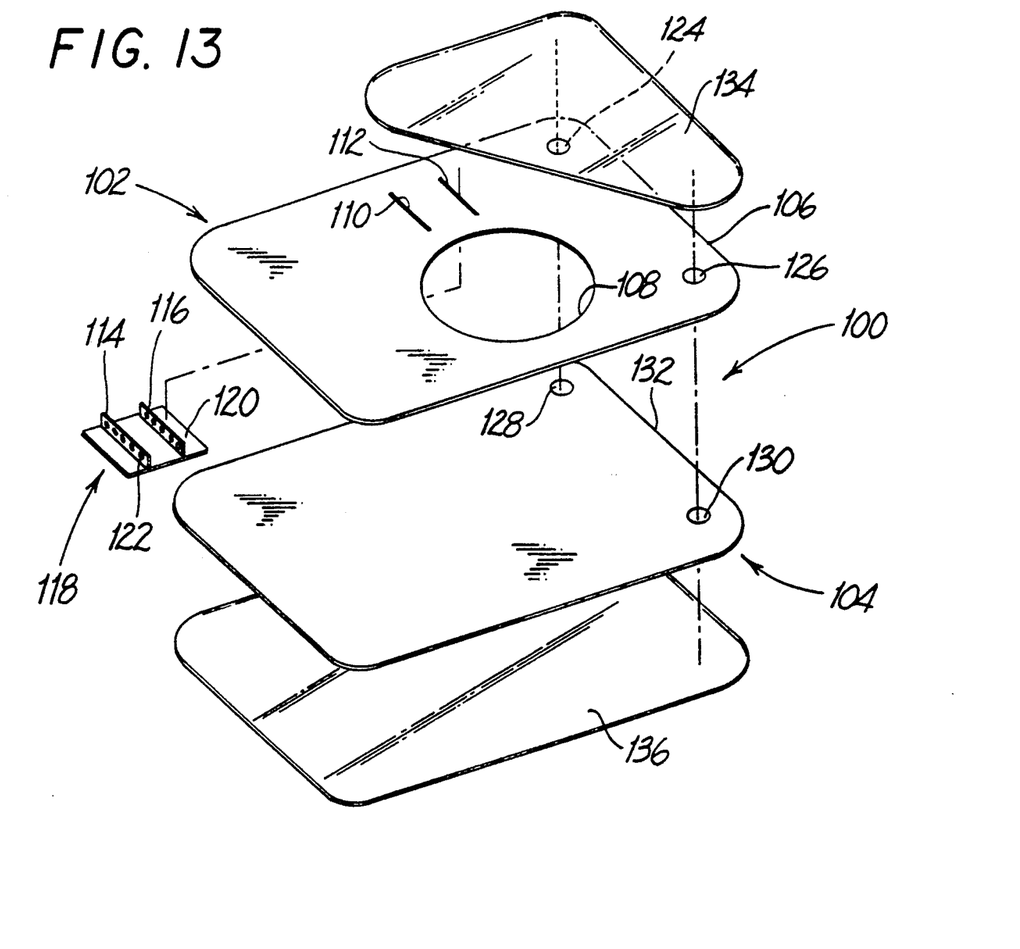
FIG. 13 is an exploded perspective view of the suture retainer package shown in FIG. 12.

A third embodiment of the suture retainer package of the subject invention is illustrated in FIGS. 12-21 and is designated generally by reference numeral 100. Referring to FIGS. 12 and 13, the suture retainer package 100 of the subject invention comprises a substantially planar top portion 102 and a substantially planar bottom portion 104 both of which are formed of Tyvek®, a woven material which is impervious to bacteria yet permits the passage of sterilization gas there through, or a material having an adhesive coating.

The top portion 102 of retainer package 100 has a radial distal edge 106 and is provided with a circular loading port 108 defining a radially unobstructed passageway through which at least one resilient surgical suture 96 arranged in a coil configuration and having a curved needle 111 affixed at one end may be loaded into the retainer package 100. In addition, a pair of spaced apart slots 110 and 112 are provided in top portion 102 for receiving the arms 114 and 116 respectively, of a plastic needle park member 118. Needle park 118 further comprises a base 120 from which arms 114 and 116 depend upwardly. Arms 114 and 116 are each provided with a plurality of spaced apart apertures 122 through which curved surgical needles 111 may be extended to be supported therein for ready removal. Additionally, a pair of spaced apart apertures 124 and 126 are provided adjacent the radial distal edge 106 of top portion 102 for permitting attachment of a protective cover. Bottom portion 104 is similarly provided with a pair of spaced apart apertures 128 and 130. More particularly, the retainer package 100 includes a two piece needle protector made of styrene comprising a triangular top member 134 and a rectangular bottom member 136 which may be sonically welded to one another through apertures 126 and 124 in top portion 102 and apertures 128 and 130 in bottom portion 104. The top member 134 is arranged so that if may be lifted to access the surgical needle 98 maintained in needle park 118.

Figure 14:
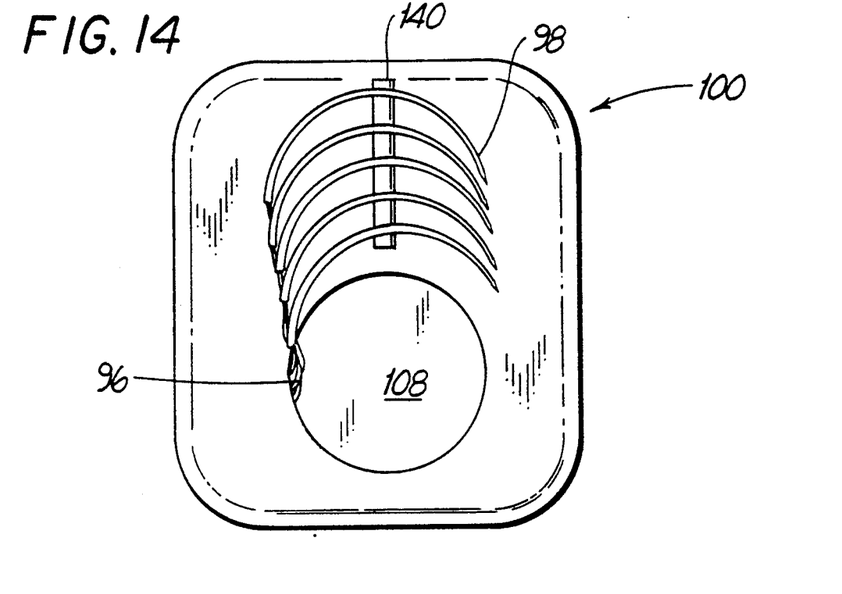
FIG. 14 is top plan view of an alternate embodiment of the suture retainer package shown in FIG. 12.

Referring to FIG. 14, in an alternate embodiment of retainer package 100 a one arm needle park member 140 may be provided. Surgical needles 98 affixed at the end of sutures 96 may be securely maintained in needle park 140 for ready removal with a surgical instrument. It may be readily apparent that other configurations of needle park structures can be employed with this retainer package.

Figure 15:
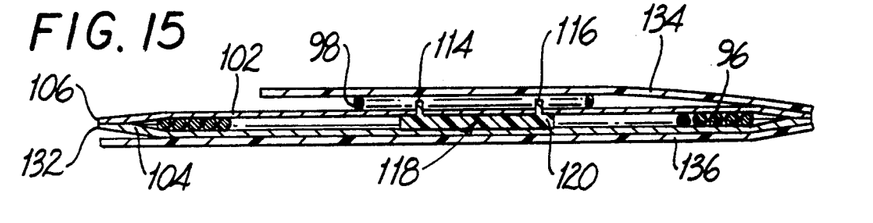
FIG. 15 is a cross-sectional view taken along line 15—15 in FIG. 12 illustrating the suture retainer package in FIG. 12.

Turning now to FIG. 15, suture retainer package 100 is constructed by placing needle park member 118 between top portion 102 and bottom portion 104 in such a manner as permit the arms 114 and 116 to extend through apertures 110 and 112 respectively. Thereupon the base portion 120 of needle park 118 is sandwiched between top portion 102 and bottom portion 104. In that instance, base portion 120 maintains adequate spacing between the top portion 102 and bottom portion 104 to provide an unobstructed passageway through which resilient surgical sutures can be loaded into the retainer package 100. Furthermore, top portion 102 and bottom portion 104 are sonically welded to one another at the radial distal edges 106 and 132 thereof, respectively.

Figure 16:
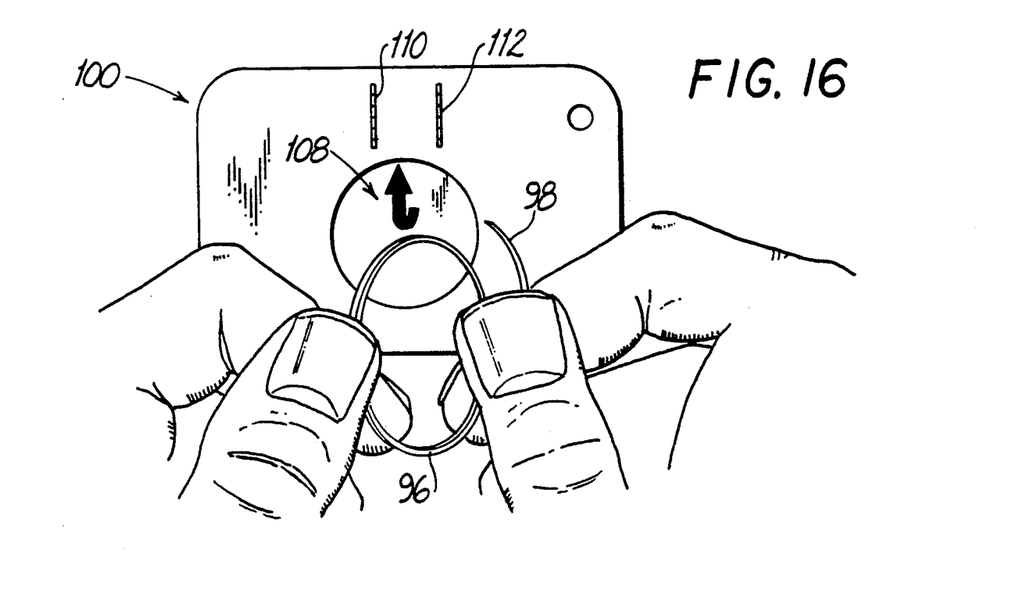
FIGS. 16-20 illustrate a method of loading a resilient surgical suture in coil configuration into the suture retainer package shown in FIGS. 12 and 13.
Figure 17:
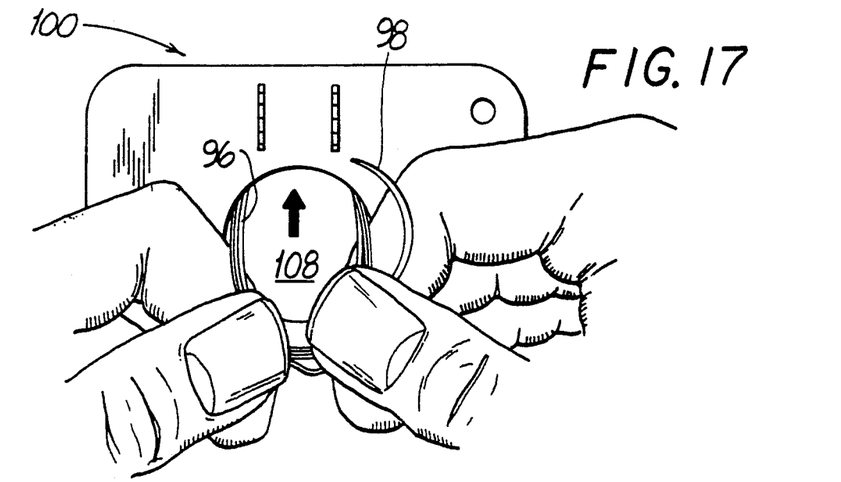
Figure 18:
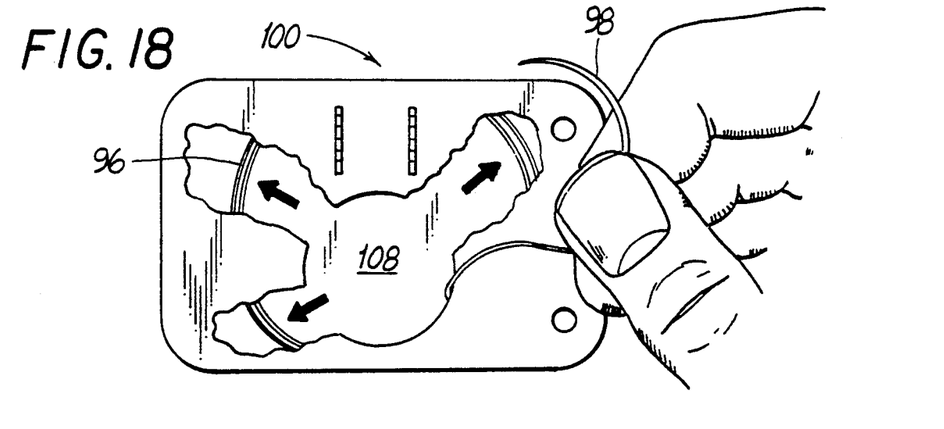
Figure 19:
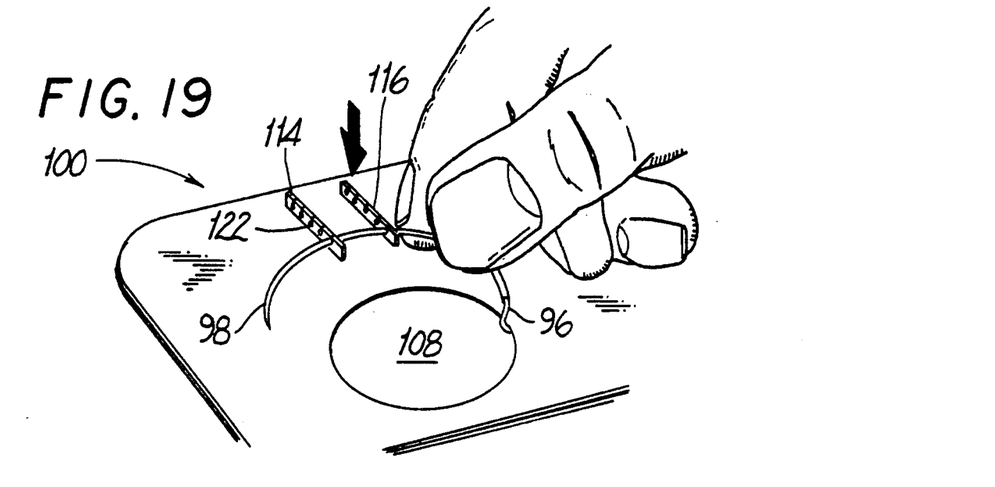

Referring to FIGS. 16–21, to load the suture retainer package 100 of the subject invention, a resilient surgical suture 96 arranged in a coil configuration and having a curved surgical needle 98 affixed at one end is directed toward the circular loading port 108 formed in the upper member 102 as illustrated by the indicator arrow in FIG. 16. Subsequently, the surgical suture coil 96 is inserted into the circular loading port 108 as illustrated by the indicator arrow in FIG. 17. Thereupon, while grasping the curved surgical needle 98 the resilient surgical suture coil 96 is permitted to uncoil and expand radially outward within the retainer package 100 as illustrated by the indicator arrow in FIG. 18. The curved surgical needle 98 may then be inserted into needle park 118 by urging the needle downwardly into the apertures 122 formed in the arms 114 and 116 of needle park 118 as illustrated by the indicator arrows in FIG. 19.

Figure 20:
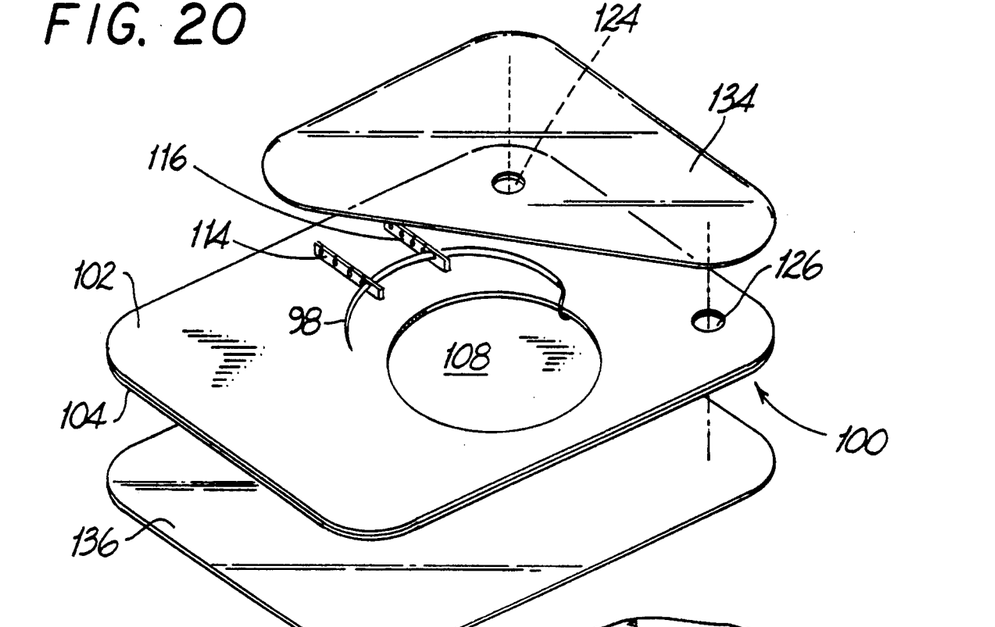

Turning now to FIG. 20, once the surgical suture has been loaded into the retainer package 100 the needle protector may be mounted to the package. More particularly, the top member 134 and the bottom member 136 of the needle protector may be sonically welded to one another by passing a weldment through the apertures provided in the package 100.

Figure 21:
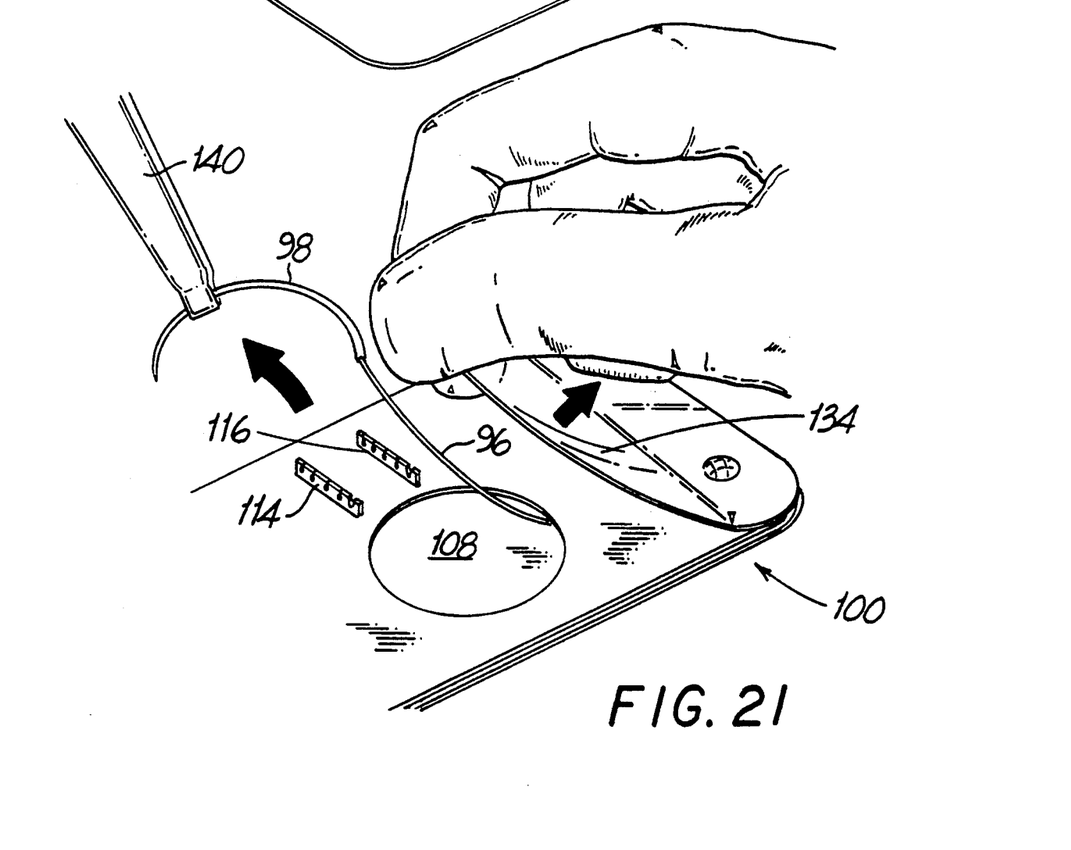
FIG. 21 illustrates a method of removing a resilient surgical suture from the retainer package shown in FIG. 12.

Turning now to FIG. 21, in order to remove a surgical suture 96 from the retainer package 100 the top portion 134 of the needle protector cover may be lifted as illustrated by the indicator arrow so as to uncover the needle park 118 with the curved surgical needle 98 maintained therein. At such a time, a needle 98 may be grasped with a pair of forceps 140 and lifted from needle park 118 as illustrated by the indicator arrow and thereupon, the resilient surgical suture 96 may be drawn from the suture retainer package 100.

Although the subject invention has been described with respect to preferred embodiments, it is apparent that several changes may be made to the invention without departing from the spirit and scope of the invention.

What is claimed is:

1. A suture retainer package for receiving at least one resilient suture in a coil configuration comprising:
   a peripheral suture retainer means having at least a top and a bottom portion being substantially closed at a radially distal edge, said top portion having a loading port formed therein defining a radially unobstructed passageway for receiving said at least one resilient suture coil into said peripheral suture retainer means; and
   needle park means associated with said suture loading port.

2. A suture retainer package as recited in claim 1, wherein said needle park means are associated with said top portion of said peripheral suture retainer means.

3. A suture retainer package as recited in claim 1, wherein needle park means are provided on said bottom portion of said peripheral suture retainer means.

4. A suture retainer package for receiving at least one resilient suture in a coil configuration comprising:
   a peripheral suture retainer means having at least a top and a bottom portion being substantially closed at a radially distal edge, said top portion having a loading port formed therein defining a radially unobstructed passageway for receiving said at least one resilient suture coil into said peripheral suture retainer means; and
   needle park means provided on said bottom portion of said peripheral suture retainer means, wherein said needle park means are disposed on a platform extending radially into said loading port.

5. A suture retainer package for receiving at least one resilient suture in a coil configuration comprising:
   a top portion having an upstanding peripheral wall, a radially inward extending upper wall depending from said peripheral wall and a radially outward extending lower wall depending from said peripheral wall, said upstanding peripheral wall forming a loading port defining a radially unobstructed passageway for receiving said at least one resilient suture coil;

a bottom portion mounted to the lower wall of said top portion at a radially distal edge to form a retaining channel; and needle park means provided on said bottom portion, said needle park means extending upwardly into said loading port;

6. A suture retainer package as recited in claim 5, wherein said upstanding peripheral wall is of elliptical configuration.

7. A suture retainer package as recited in claim 5, wherein said needle park means comprises a sponge member.

8. A suture retainer package as recited in claim 5, wherein said top portion is mounted to said bottom portion by applying sonic weldments at said radially distal edge.

9. A suture retainer package for receiving at least one resilient suture in a coil configuration comprising:

a substantially planar top portion having a radially distal edge and having a circular loading port formed therein defining a radially unobstructed passageway for receiving said at least one resilient suture coil;

a substantially planar bottom portion mounted to said top portion along the entirety of said radial distal edge to form a retaining channel; and separate needle park means mounted to said top portion and including at least one arm having means for securing at least one surgical needle 10. A suture retainer package as recited in claim 9, wherein said top portion and said bottom portion are mounted to one another by applying sonic weldments along said radial distal edge.

11. A suture retainer package as recited in claim 9, wherein said needle park means are provided in said top member adjacent the periphery of said circular loading port.

12.

13. A suture retainer package as recited in claim 12, wherein a protective cover is affixed to said package covering said needle park means.

14. A suture retainer package as recited in claim 13, wherein said protective cover is made of styrene.

15. A suture retainer package for receiving at least one resilient suture in a coil configuration comprising:

a substantially planar top portion having a radially distal edge and having a circular loading port formed therein defining a radially unobstructed passageway for receiving said at least one resilient suture coil; and a substantially planar bottom portion mounted to said top portion along said radial distal edge to form a retaining channel, wherein said top portion and said bottom portion are made of a woven material impervious to bacteria.

16. A suture retainer package for receiving at least one resilient suture in a coil configuration comprising:

an annular channel member having a substantially C-shaped cross-section including an upstanding peripheral wall forming a loading port which defines a radially unobstructed passageway for receiving said at least one resilient suture coil into said annular channel member; and needle park means associated with said suture package, said needle park means extending into said loading port.

17. A suture retainer package as recited in claim 16, wherein said upstanding peripheral wall is of circular configuration.

18. A suture retainer package as recited in claim 16, wherein a planar platform extends integrally from said peripheral wall into said loading port.

19. A suture retainer port as recited in claim 18, wherein said needle park means are provided on said planar platform.

20. A suture retainer package as recited in claim 19, wherein said needle park means is a sponge member.

21. A method of loading at least one resilient suture in a coil configuration into a peripheral suture retainer means, said retainer means having at least a top and a bottom portion being closed at a radially distal edge, said top portion having a loading port formed therein defining a radially unobstructed passageway for receiving said at least one suture coil into said suture retainer means, said method comprising the steps of:

inserting said at least one resilient suture coil into said loading port; and causing said at least one resilient suture to uncoil and expand radially outward into said suture retainer means.

22. A method of loading at least one resilient armed suture in a coil configuration into a suture retainer package, said package comprising an annular channel member having a substantially C-shaped cross-section including an upstanding peripheral wall forming an annular loading port which defines a radially unobstructed passageway for receiving said at least one resilient suture coil into said annular channel member, said method comprising the steps of:

inserting said at least one resilient suture coil concentrically into said annular loading port; and causing said at least one resilient suture to uncoil and expand radially outward into said annular channel member.

23. A method of loading as recited in claim 23, further comprising the step of inserting a needle into said needle park means provided on a platform extending radially inward from said upstanding peripheral wall.

24. A method of loading at least one armed resilient suture in a coil configuration into a suture retainer package, said suture retainer package having a top portion and a bottom portion, said top portion having a loading port formed therein defining a radially unobstructed passageway for receiving said at least one suture coil into said suture retainer package, said method comprising the steps of:

inserting said at least one resilient suture coil into said loading port; and causing said at least one resilient suture to uncoil and expand radially outward into said suture retainer package in such a manner so as to be held within said retainer package for ready removal.

25. A method of loading as recited in claim 24, further comprising the step of inserting a needle into a needle park associated with said top portion of said package.

26. A method of loading as recited in claim 25, further comprising the step of inserting a needle into a needle park provided on said bottom portion of said package within said loading port.

* * * * *

UNITED STATES PATENT AND TRADEMARK OFFICE
CERTIFICATE OF CORRECTION

PATENT NO. : 5,228,565
DATED : July 20, 1993
INVENTOR(S) : Hans-Jurgen F. Sinn It is certified that error appears in the above-identified patent and that said Letters Patent is hereby corrected as shown below:

Column 9, line 40, after "12." insert --A suture retainer package as recited in claim 11, wherein said top portion includes at least one engaging slot disposed adjacent the periphery of said loading port, said needle park means having at least one arm depending orthogonally from a base, said at least one arm extending through said at least one engaging slot in said top portion to be maintained therein.--

Signed and Sealed this

Fifteenth Day of February, 1994

*Attest:*

BRUCE LEHMAN

*Attesting Officer*  Commissioner of Patents and Trademarks